(12) United States Patent
Raynor

(10) Patent No.: US 7,273,633 B2
(45) Date of Patent: Sep. 25, 2007

(54) SENSORS

(75) Inventor: Jeffrey Raynor, Edinburgh (GB)

(73) Assignee: STMicroelectronics Ltd., Buckinghamshire (GB)

( * ) Notice: Subject to any disclaimer, the term of this patent is extended or adjusted under 35 U.S.C. 154(b) by 30 days.

(21) Appl. No.: 11/018,979

(22) Filed: Dec. 21, 2004

(65) Prior Publication Data

US 2005/0151148 A1 Jul. 14, 2005

(30) Foreign Application Priority Data

Dec. 22, 2003 (EP) .................................. 03258136

(51) Int. Cl.
*C12M 1/34* (2006.01)
*B05D 3/00* (2006.01)
(52) U.S. Cl. ..................................... 427/2.11
(58) Field of Classification Search ............. None
See application file for complete search history.

(56) References Cited

U.S. PATENT DOCUMENTS

| | | | |
|---|---|---|---|
| 6,159,681 A | 12/2000 | Zebala | 435/4 |
| 2003/0064316 A1 | 4/2003 | Zebala | 430/270.1 |

FOREIGN PATENT DOCUMENTS

| | | | |
|---|---|---|---|
| DE | 10139742 | | 3/2003 |
| EP | 0368482 | | 5/1990 |
| WO | WO 99/61653 | * | 12/1999 |
| WO | 00/33084 | | 6/2000 |

OTHER PUBLICATIONS

Hanazato et al., Integrated Multi-Biosensors Based on an Ion-Sensitive Field-Effect Transistor using Photolithographic Techniques, IEEE Transactions on Electron Devices, IEEE Inc., New York, US, vol. 36, No. 7, Jul. 1, 1989, pp. 1303-1310.
Popovic et al., Technique for Monolithic Fabrication of Microlens Arrays, Applied Optics, Optical Society of America, Washington, US, vol. 27, No. 7, Apr. 1, 1988, pp. 1281-1284.

* cited by examiner

*Primary Examiner*—Erma Cameron
(74) *Attorney, Agent, or Firm*—Lisa K. Jorgenson; Allen, Dyer, Doppelt, Milbrath & Gilchrist, P.A.

(57) ABSTRACT

A method for forming a sensor is provided, together with a sensor formed according to the method. Photoresist material is deposited on a surface of the sensor, and is then patterned and etched to form an array of microlens structures. The structures are spaced close together in a predetermined pattern so that when a reflow process is performed, the structures melt and coalesce to form a barrier. The barrier defines a region for constraining or channeling the flow of reagent and analyte samples used in bio-optical sensors.

13 Claims, 6 Drawing Sheets

SENSORS

FIELD OF THE INVENTION

The present invention relates to sensors, and in particular, to a method of forming a sensor and a sensor produced in accordance with that method.

BACKGROUND OF THE INVENTION

Bio-optical sensors detect photo-emissive chemical reactions between an analyte and a reagent. Improved bio-optical sensors have a number of different reagents to enable them to detect the presence/concentration of several analytes. During the manufacture of such sensors, it is necessary to locate and separate the reagents, and during their operation, it is necessary to guide the sample containing the analyte over the sensor sites.

The sites should be mechanically isolated. Suitable structures may be patterned and etch, either on the silicon of the sensor surface or by making trenches in the silicon itself. However, these methods currently require special technology, processing and equipment which add to the manufacturing cost.

When forming a structure on the surface of the sensor, materials such as polyimide are typically used because they provide good patterning and etching properties. While found in a research laboratory, these chemicals are not usually found in a production environment. The introduction of these materials requires a modification to normal production processes.

SUMMARY OF THE INVENTION

In view of the foregoing background, an object of the invention is to provide a method for forming 3D structures reliably and inexpensively on the surface of a sensor. The method may be easily incorporated into existing manufacturing processes.

According to a first aspect of the invention, a method for forming a sensor comprises forming an array of pixels in a substrate, and forming a barrier of photoresist material on a surface of the array of pixels. The barrier may define at least one region for constraining a bio-optical reagent or analyte therein.

Forming the barrier may comprise depositing photoresist material on the surface of the array of pixels, patterning and etching the photoresist material so that a plurality of discrete photoresist material volumes are formed, and deforming the plurality of photoresist material volumes so that adjacent photoresist material volumes are joined together for forming the barrier.

The deforming may comprise heating the plurality of photoresist material volumes. The photoresist material may be patterned and etched so that the plurality of photoresist material volumes are spaced apart a predetermined distance, with the predetermined distance resulting in the adjacent photoresist material volumes being joined together when heated. The predetermined distance may be equal to or less than 2 µm, for example.

The method may further comprise depositing a bio-optical reagent in the at least one region. The at least one region may comprise a plurality of regions, and the method may further comprise depositing different types of reagents in the plurality of regions.

According to a second aspect of the invention, a sensor comprises a substrate, an array of pixels in the substrate, and a barrier of photoresist material on a surface of the array of pixels. The barrier may define at least one region for constraining a bio-optical reagent or analyte therein. The sensor may be a bio-optical sensor.

BRIEF DESCRIPTION OF THE DRAWINGS

Specific embodiments of the invention shall now be described, by way of example only, with reference to the accompanying drawings, in which.

DETAILED DESCRIPTION OF THE PREFERRED EMBODIMENTS

Figure 1:
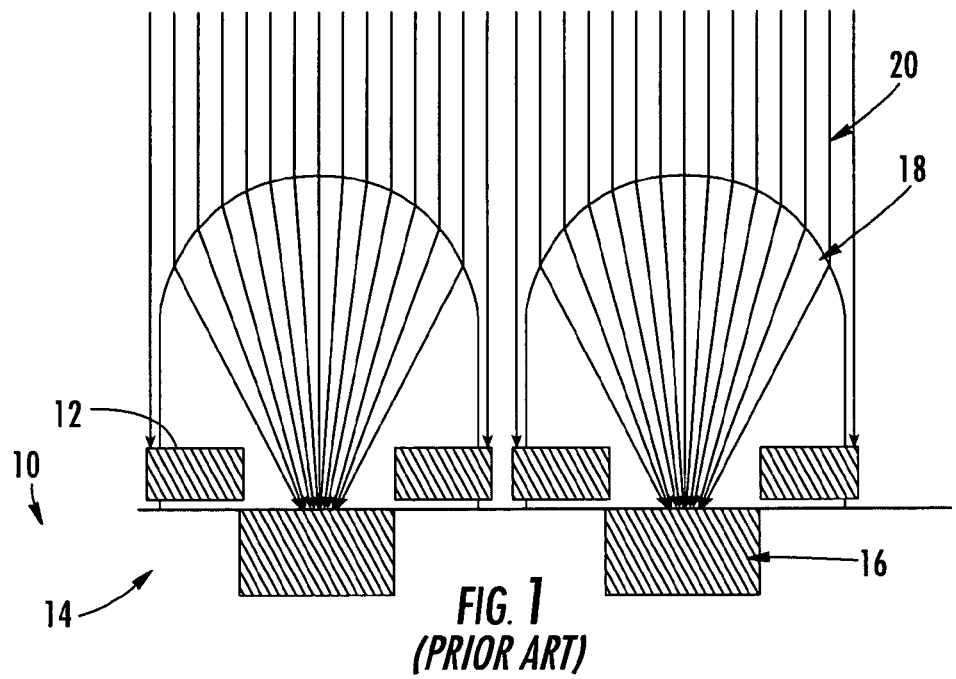
FIG. 1 shows the prior art structure and function of microlenses.

Microlenses are incorporated on image sensors to overcome the sensitivity loss caused by the circuitry which blocks light. FIG. 1 illustrates the operation of microlenses. A sensor 10 comprises circuitry 12 that overlies a substrate 14 and blocks incident light. This means that the sensor 10 is only sensitive to light at certain sensitive areas 16 of the substrate 14. To overcome the loss of light that would normally be blocked by the circuitry 12, a microlens 18 focuses incident light, represented by light rays 20, onto the sensitive areas 16.

Microlenses are implemented on a large number of image sensors. They are distributed over the image array (one microlens per pixel). The technology to produce microlenses is commonly found in high-volume silicon manufacture.

Figure 2:
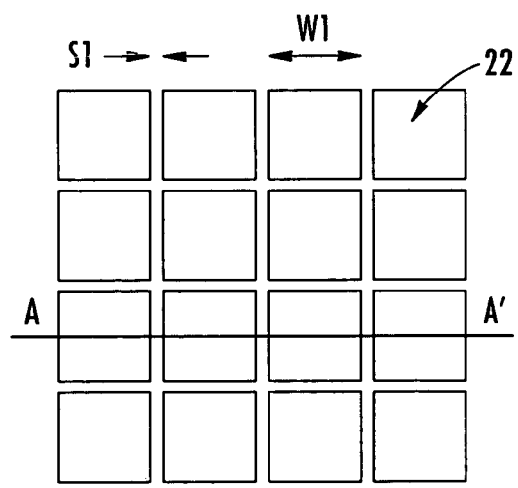
FIGS. 2 and 3 show plan and cross-sectional views of prior art microlenses before a reflow step is applied.
Figure 3:
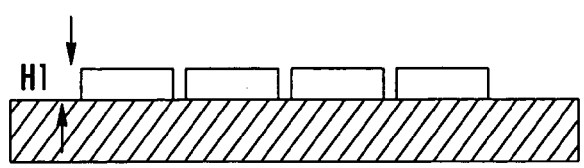

The microlens is formed by depositing a photoresist material on the surface of the sensor. It is patterned using photolithography (aligned to the pixel structure) and etched, resulting in a structure illustrated in FIGS. 2 and 3. A grid of volume portions 22 are formed, having a width W1 and spaced apart by a distance S1. FIG. 3 shows a cross-section along A-A'. Each volume portion has a height H1.

The microlenses are typically matched to the pitch of the sensor, i.e., the sensor pixel pitch is equal to S1+W1. Typically this is between 4 µm-10 µm.

Figure 4:
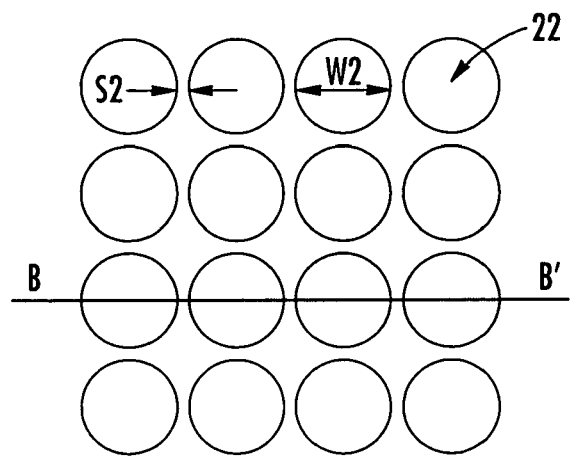
FIGS. 4 and 5 show plan and cross-sectional views of prior art microlenses after the reflow step is applied.
Figure 5:
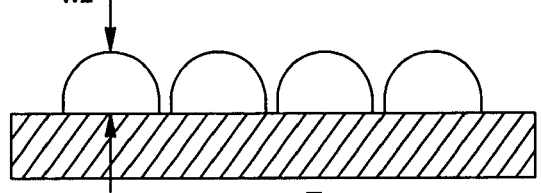

The photoresist is then deformed by heating it until it melts, in what is referred to as a reflow process. This is carried out at a relatively low temperature (e.g., 200° C.)—lower than the typical manufacturing temperature for the silicon so that the silicon is undamaged. When the microlens material melts, surface tension causes it to produce a hemisphere. FIGS. 4 and 5 illustrate the microlenses after being deformed by the heating process. Volume portions 22 have a width W2 and are spaced apart by a distance S2. FIG. 5 shows a cross-section along B-B'. Each volume portion 22 has a height H2.

During this process, the volume and pitch between the microlenses remains unchanged. However, the shape and height does change, where W2>W1 and S2<S1. H1 will determine H2, from which the curvature and the focusing properties of the microlens are derived.

The initial spacing S1 between microlenses is critical. For construction of an efficient microlens, if S1 is too large, the light-collecting efficiency of the microlens will be reduced. However, if S1 is too small, two adjacent microlenses will touch and surface tension will prevent the microlens from forming correctly.

The term adjacent in this context is taken to mean that two microlenses correspond to adjacent pixels on the array of the sensor. Two microlenses may be considered as being adjacent if they are the nearest neighbors, and there is a risk of them merging when they deform under heat. S1 will ideally be as small as possible. However, for the formation of microlenses, practical values are 1 µm-2 µm.

The microlens formation process can be misused to produce simple, but effective, 3-dimensional structures on the surface of the silicon. Instead of aiming to space the microlenses sufficiently far apart to prevent the merging of adjacent lenses, the microlens volume portions are deliberately formed close together so that they join up during reflow.

Figure 6:
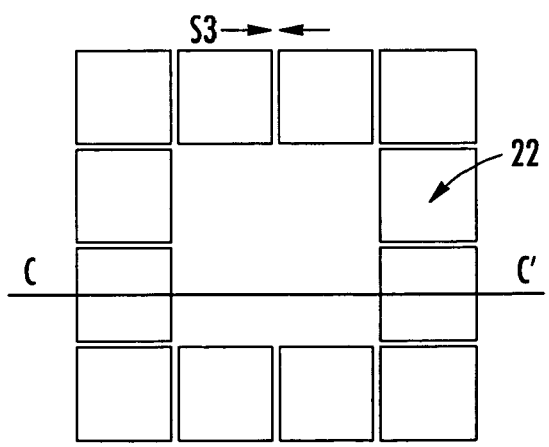
FIGS. 6 and 7 show plan and cross-sectional views of a first embodiment of the present invention before a reflow step is applied.
Figure 7:
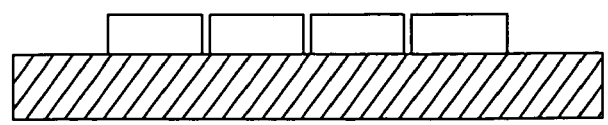

FIGS. 6-9 illustrate a first embodiment of the present invention. As shown in FIG. 6, photoresist volume portions 22 are spaced apart by a distance S3, where S3<S1, and are formed in a defined shape, namely a ring. The value of S3 is chosen to ensure that adjacent volume portions 22 merge together during reflow. S3 could even be made as low as zero.

When S3 is zero, a reflow step is not necessary to ensure that a barrier of photoresist material is formed for defining a region suitable for constraining bio-optical reagent or analyte sample materials. However, a reflow step can still be performed to ensure that the edges and walls of the patterned regions and channels are smoother. The increased smoothness helps to reduce resistance to the flow of bio-optical reagent or analyte sample materials.

Figure 8:
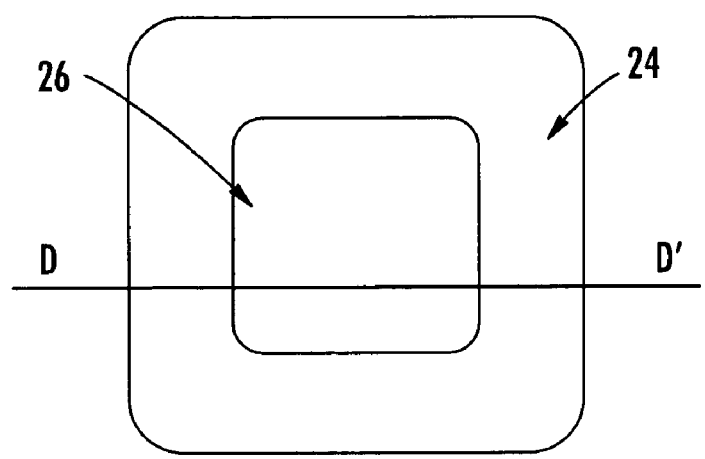
FIGS. 8 and 9 show plan and cross-sectional views of the first embodiment after the reflow step is applied.
Figure 9:
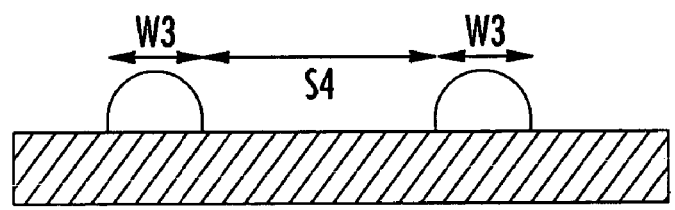

During the heating process the microlens material will melt. As the squares are closed, under the influence of gravity, the material will touch and surface tension will cause them to join up. FIG. 8 shows the result—there is an annulus 24 of microlens material with a void 26 in the middle. FIG. 9 shows a cross-section along line D-D' of FIG. 8. The annulus 24 has a width W3, with the void 26 having a dimension S4.

The void 26 shown in FIGS. 8 and 9 allows accurate deposition of the reagent during manufacture of a bio-optical sensor. The dimension S4 of the void 26 is independent of the width W3 of the microlens, but is usually an integral number of pixels. A typical value for W3 is 5 µm and for S4 is 50 µm.

Figure 10:
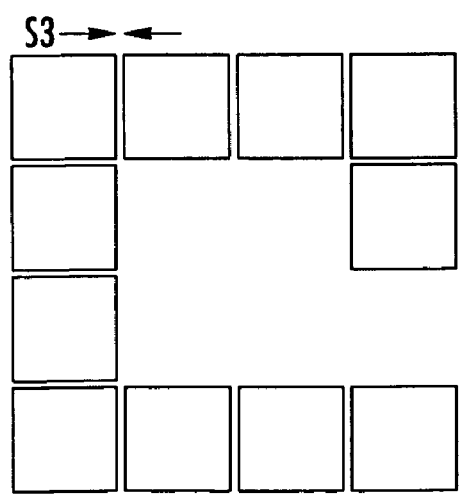
FIGS. 10 and 11 show plan views of a second embodiment of the present invention before and after a reflow step is applied.
Figure 11:
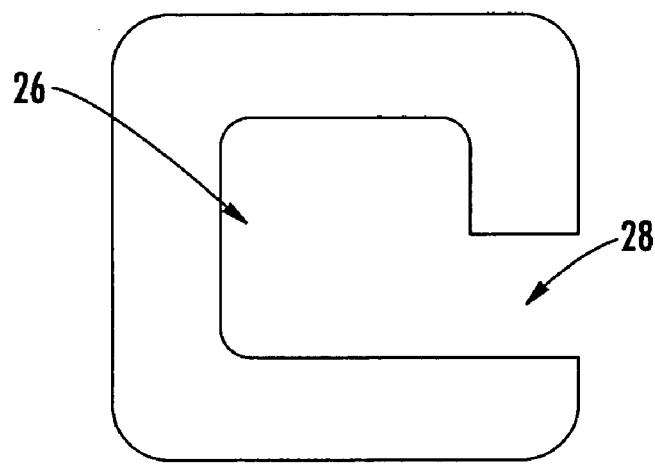
Figure 12:
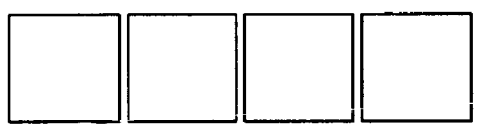
FIGS. 12 and 13 show plan views of a third embodiment of the present invention before and after a reflow step is applied.
Figure 12:
Figure 13:
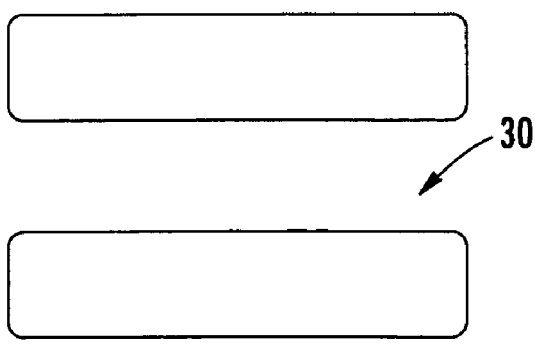

In addition to forming an annulus/void, the idea can be extended to produce other shapes. FIGS. 10 and 11 illustrate a second embodiment of the invention, where one microlens is omitted from the arrangement shown in FIG. 6. This produces an entrance 28 to the void 26, producing a cup shape. FIGS. 10 and 11 show the microlens layouts before and after reflow. FIGS. 12 and 13 show a third embodiment for forming a channel 30.

Figure 14:
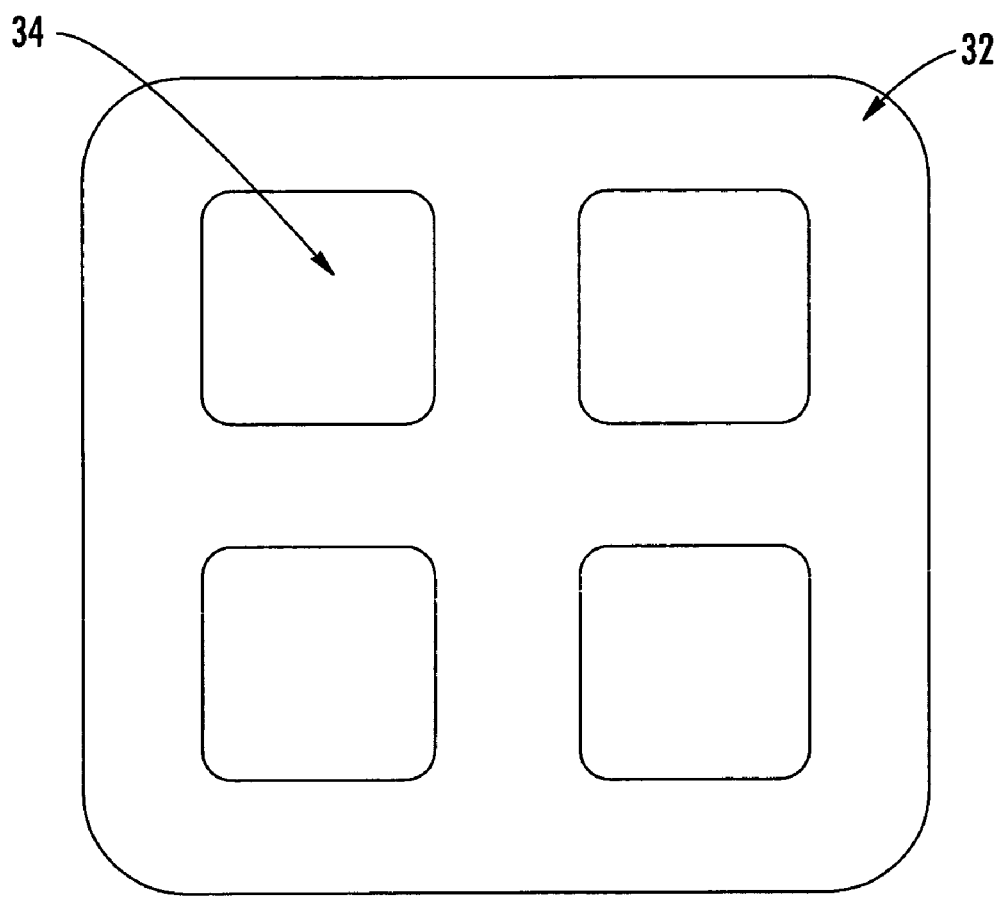
FIG. 14 shows a plan view of a fourth embodiment of the present invention.

More complex shapes can also be constructed. FIG. 14 shows a fourth embodiment, where four annuli as shown in FIG. 6 are combined to form a microlens structure 32 comprising four sites 34.

With this structure, four different reagents could be deposited at each of the four sites 34. The microlens material 32 provides an effective barrier between the sites to isolate reagents located in the neighboring sites 34. This sensor could then provide the sensing and/or detection of up to four different chemicals in the analyte.

Figure 15:
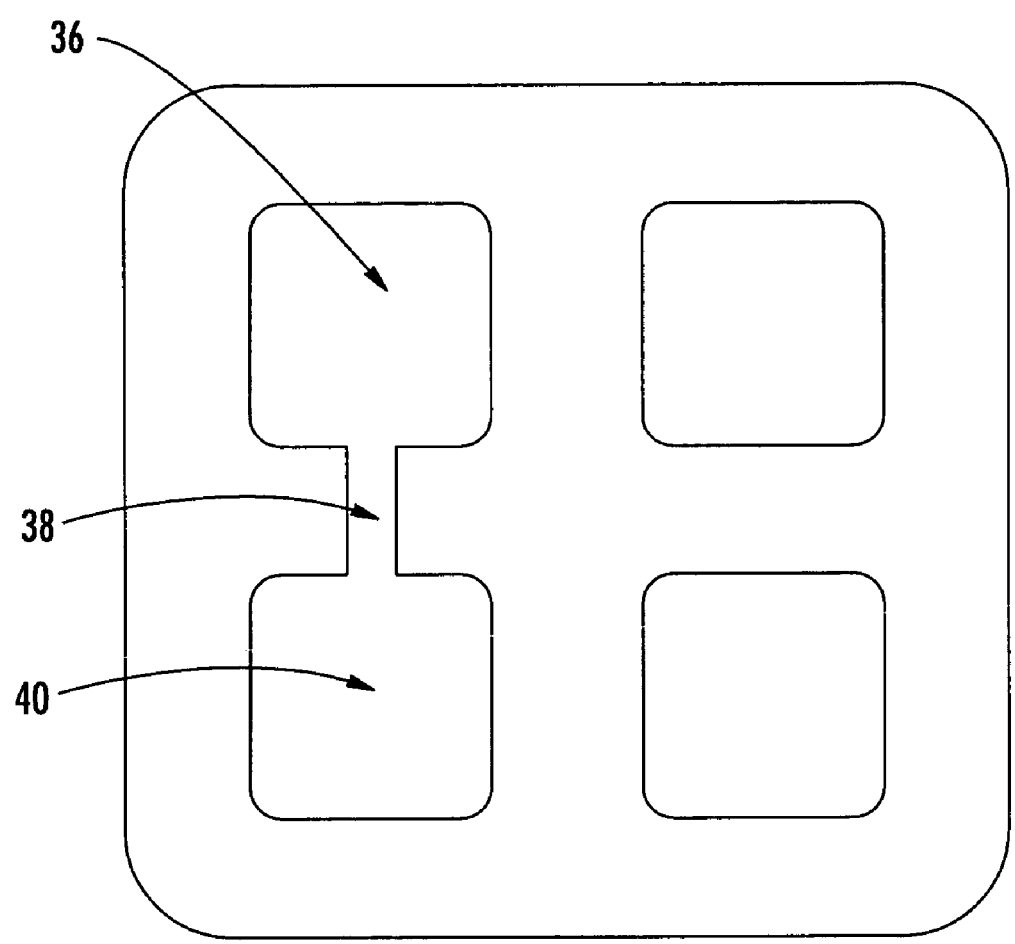
FIG. 15 shows a plan view of a fifth embodiment of the present invention.

FIG. 15 shows a fifth embodiment, where two sites 36, 40 are connected by a channel 38. The connection allows the analyte to flow between different sites.

It will be appreciated that the regions formed by the particular shapes and formations referred to above are only a very few of a large number of regions that can be formed using the techniques of the present invention, and the present invention is in no way to be considered as being limited to these particular regions.

The principles of the invention, when applied to bio-optical sensor systems, allow both accurate deposition of a reagent during manufacture of the system and also the production of channels and guides to assist the flow of the analyte during operation of the system.

It is also to be recognized that the top surface of the sensor is usually formed from silicon nitride to protect the device. This material can also be patterned and etched to provide similarly defined regions that serve similar purposes as described above.

The invention is compatible with existing manufacturing processes, and does not incur a cost penalty to introduce nor is its processing complex or time consuming. This reduces the overall cost of production of the sensors. Various improvements and modifications may be made to the above without departing from the scope of the invention.

That which is claimed is:

1. A method for forming a sensor comprising:
   forming an array of pixels in a substrate; and
   forming a barrier of photoresist material on a surface of the array of pixels by
      depositing photoresist material on the surface of the array of pixels,
      patterning and etching the photoresist material so that a plurality of discrete photoresist material volumes are formed, and
      deforming the plurality of photoresist material volumes so that adjacent photoresist material volumes are joined together for forming the barrier;
   the barrier defining at least one region for constraining a bio-optical reagent or bio-optical analyte therein.

2. A method according to claim 1, wherein the deforming comprises heating the plurality of photoresist material volumes.

3. A method according to claim 2, wherein the photoresist material is patterned and etched so that the plurality of photoresist material volumes are spaced apart a predetermined distance, the predetermined distance resulting in the adjacent photoresist material volumes being joined together when heated.

4. A method according to claim 3, wherein the predetermined distance is equal to or less than 2 µm.

5. A method according to claim 1, further comprising depositing a bio-optical reagent in the at least one region.

6. A method according to claim 5, wherein the at least one region comprises a plurality of regions; and further comprising depositing a different type of reagent in each of the plurality of regions.

7. A method according to claim 1, wherein the sensor is a bio-optical sensor.

8. A method for forming a bio-optical sensor comprising:
  forming an array of pixels in a substrate; and
  forming a photoresist material layer on a surface of the array of pixels;
  removing a portion of the photoresist material layer for forming a plurality of discrete photoresist material volumes; and
  deforming the plurality of photoresist material volumes so that adjacent photoresist material volumes are joined together for forming a barrier, the barrier defining at least one region for constraining a bio-optical reagent or bio-optical analyte therein.

9. A method according to claim 8, wherein the deforming comprises heating the plurality of photoresist material volumes.

10. A method according to claim 9, wherein the plurality of photoresist material volumes are spaced apart a predetermined distance, the predetermined distance resulting in the adjacent photoresist material volumes being joined together when heated.

11. A method according to claim 10, wherein the predetermined distance is equal to or less than 2 μm.

12. A method according to claim 8, further comprising depositing a bio-optical reagent in the at least one region.

13. A method according to claim 12, wherein the at least one region comprises a plurality of regions; and further comprising depositing a different type of reagent in each of the plurality of regions.

* * * * *